(12) United States Patent
Hua et al.

(10) Patent No.: US 9,181,167 B2
(45) Date of Patent: Nov. 10, 2015

(54) CHEMICALLY-MODIFIED GRAPHENE AND METHOD FOR PRODUCING THE SAME

(75) Inventors: Mu-Yi Hua, Kwei-Shan (TW);
Shi-Liang Chen, Zhongli (TW);
Hsiao-Chien Chen, Taichung (TW);
Rung-Ywan Tsai, Zhudong Township (TW); Wu-Shiung Feng, Taipei (TW);
Ming-Jer Jeng, New Taipei (TW)

(73) Assignee: Chang Gung University, Tao-Yuan (TW)

( * ) Notice: Subject to any disclaimer, the term of this patent is extended or adjusted under 35 U.S.C. 154(b) by 0 days.

(21) Appl. No.: 13/617,672

(22) Filed: Sep. 14, 2012

(65) Prior Publication Data

US 2013/0137894 A1  May 30, 2013

(30) Foreign Application Priority Data

Nov. 30, 2011  (TW) .............................. 100143962 A

(51) Int. Cl.
*C07C 51/083*  (2006.01)
*C07C 59/76*  (2006.01)

(52) U.S. Cl.
CPC ............... *C07C 51/083* (2013.01); *C07C 59/76* (2013.01)

(58) Field of Classification Search
None
See application file for complete search history.

(56) References Cited

U.S. PATENT DOCUMENTS 4,895,984 A *  1/1990  Eggersdorfer et al. ....... 568/319
7,816,564 B2 *  10/2010  Balaban et al. ............... 568/397

FOREIGN PATENT DOCUMENTS

TW  201033118 A1  9/2010

OTHER PUBLICATIONS

Chua et al. Chem. Soc. Rev., 2013, 42, 3222-3233.*
Over Bae et al. Advanced Materials Research, 2010, 113-116.*
Britton et al. J. Electroanal. Chem. 172, 1984, 189-200.*
Hsaio, et al., "Preparation of Covalently Functionalized Graphene Using Residual Oxygen-Containing Functional Groups", ACS Applied Materials & Interfaces, vol. 2, No. 11, 2010.

* cited by examiner

*Primary Examiner* — Yong Chu
*Assistant Examiner* — Ana Z Muresan
(74) *Attorney, Agent, or Firm* — Cesari and McKenna, LLP

(57) ABSTRACT

A chemically-modified graphene includes a graphene layer and a plurality of functional groups that are grafted to the graphene layer and each of which is represented by —CO—R—COOH, wherein R is an optionally substituted $C_1$-$C_5$ alkylene group or an optionally substituted $C_1$-$C_5$ alkenylene group. A method for producing a chemically-modified graphene includes subjecting a cyclic anhydride and graphite to a Friedel-Crafts reaction in the presence of a Lewis acid.

3 Claims, 6 Drawing Sheets

CHEMICALLY-MODIFIED GRAPHENE AND METHOD FOR PRODUCING THE SAME

CROSS-REFERENCE TO RELATED APPLICATION

This application claims priority of Taiwanese application no. 100143962, filed on Nov. 30, 2011.

BACKGROUND OF THE INVENTION

1. Field of the Invention

This invention relates to a graphene and a method for producing the same, more particularly to a chemically-modified graphene and a method for producing the same.

2. Description of the Related Art

Graphene has a single layer of carbon atoms that are densely packed in a two-dimensional honeycomb lattice. Graphene has application potential in the fields of transparent electrodes, thermal interface material, and electrochromic devices because of excellent electrically conductive and thermally conductive properties thereof.

I. L. Aksay et. al. disclosed a method for producing a graphene (*Chem. Mater.*, 19, 4396-4404, 2007). The method involves thermal expansion of a graphite oxide by heating the graphite oxide to a temperature of 1050° C. to generate carbon dioxide by which the graphite oxide is exfoliated to form the graphene.

M. C. Hsiao et. al. disclosed a method for producing a carboxylic acid-containing graphene (*ASC Appl. Mater. Interfaces*, 2, 3092-3099, 2010). The method involves subjecting an amine-terminated polyetheramine derivate and an epoxy group on a graphene oxide to a ring-opening grafting reaction for 24 hours to form a carboxylic acid-containing graphene derivate. However, in this method, graphite has to be oxidized to form graphite oxide before the carboxylation reaction is conducted, which is time-consuming.

E. K. Choi et. al. disclosed a method for producing an amino group-containing graphene (*Chem. Commun.*, 46, 6320-6322, 2010). The method involves exfoliation of graphite by grafting 4-aminobenzoic acid to defect sites of the graphite in poly(phosphoric acid) (PPA)/phosphorus pentoxide medium. However, because PPA has high viscosity, the grafting reaction is liable to be suppressed. Therefore, a longer reaction time and a subsequent purification step are required.

SUMMARY OF THE INVENTION

Therefore, the object of the present invention is to provide a graphene having good dispersion ability in most polar solvents and a method for producing the same that can overcome at least one of the aforesaid drawbacks of the prior art.

According to one aspect of this invention, a chemically-modified graphene comprises a graphene layer and a plurality of functional groups that are grafted to the graphene layer and each of which is represented by —CO—R—COOH. R is an optionally substituted $C_1$-$C_5$ alkylene group or an optionally substituted $C_1$-$C_5$ alkenylene group.

According to another aspect of this invention, a method for producing a chemically-modified graphene comprises subjecting a cyclic anhydride and graphite to a Friedel-Crafts reaction in the presence of a Lewis acid.

BRIEF DESCRIPTION OF THE DRAWINGS

Other features and advantages of the present invention will become apparent in the following detailed description of the preferred embodiments of this invention, with reference to the accompanying drawings, in which.

DETAILED DESCRIPTION OF THE PREFERRED EMBODIMENTS

Figure 1:
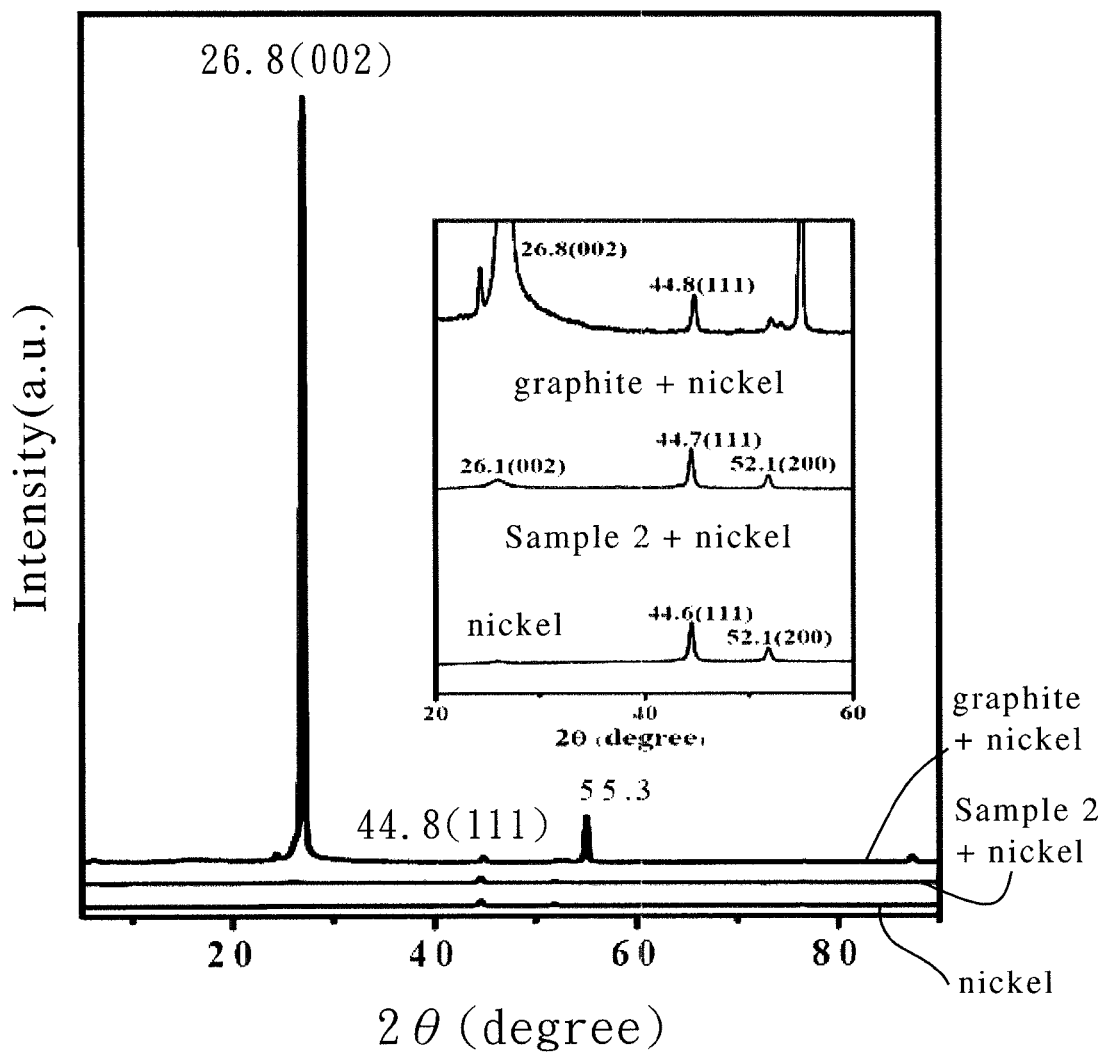
FIG. 1 shows X-ray diffraction (XRD) spectra for the graphite, Sample 2 of Example 2, and nickel, and the inset is an enlarged view at 2θ ranging from 20.0° to 60.0°.

A chemically-modified graphene of the present invention comprises: a graphene layer, and a plurality of functional groups that are grafted to the graphene layer and each of which is represented by —CO—R—COOH, in which R is an optionally substituted $C_1$-$C_5$ alkylene group or an optionally substituted $C_1$-$C_5$ alkenylene group.

Preferably, R is an optionally substituted ethylene group or an optionally substituted vinylene group.

A method for producing a chemically-modified graphene of this invention comprises: subjecting a cyclic anhydride and graphite to a Friedel-Crafts reaction in the presence of a Lewis acid.

Preferably, the cyclic anhydride is selected from the group consisting of a maleic anhydride-based compound, a succinic anhydride-based compound, and the combination thereof. In examples of the present invention, the cyclic anhydride is maleic anhydride or succinic anhydride.

Preferably, the Lewis acid is selected from the group consisting of aluminum chloride, aluminum bromide, trifluoroborane, boron trichloride, borontribromide, trimethylboron, iron(III) chloride, magnesium bromide, and combinations thereof.

Preferably, the Friedel-Crafts reaction is conducted in a polar aprotic solvent. More preferably, the polar aprotic solvent is selected from the group consisting of dimethyl sulfoxide, N-methyl-2-pyrrolidone (NMP), N, N-dimethylformamide, N, N-dimethylacetamide, and combinations thereof. In examples of the present invention, the polar aprotic solvent is NMP.

Preferably, the molar ratio of the cyclic anhydride to the Lewis acid ranges from 1:0.5 to 1:10. More preferably, the molar ratio of the cyclic anhydride to the Lewis acid ranges from 1:1 to 1:6.

Preferably, the weight ratio of the cyclic anhydride to the graphite ranges from 1:0.01 to 1:0.5.

In this invention, the Friedel-Crafts reaction includes: (a) subjecting the cyclic anhydride to a ring opening reaction in the presence of the Lewis acid so as to form a ring-opened intermediate; and (b) grafting the ring-opened intermediate to the graphite.

Preferably, step (a) is conducted at a temperature ranging from 70° C. to 120° C. More preferably, step (a) is conducted at a temperature ranging from 80° C. to 100° C.

Preferably, step (b) is conducted at a temperature ranging from 120° C. to 180° C., more preferably, from 140° C. to 170° C.

Preferably, step (b) can be conducted with ultrasonic vibration, stirring, thermal expansion, cutting, or microwave to facilitate exfoliating graphite into graphene.

This invention will be further described by way of the following examples. However, it should be understood that the following examples are solely for the purpose of illustration and should not be construed as limiting the invention in practice.

EXAMPLES

Example 1

A chemically-modified graphene of Example 1 was produced by the following steps:

(1) Graphite (50 mg) was placed in N-methyl-2-pyrrolidone (NMP, 200 ml) and was dispersed by virtue of ultrasonic vibration to obtain a graphite dispersion solution.

(2) Maleic anhydride (0.98 g, 10 mmol, commercially available from Showa Chemical Co.) was dissolved in NMP (40 ml), followed by slowly adding with aluminum chloride (1.36 g, 10 mmol) and stirring at 90° C. for 4 hours to obtain a maleic anhydride solution.

(3) After the maleic anhydride solution was heated to 160° C., the graphite dispersion solution was added dropwise into the maleic anhydride solution followed by reaction for 48 hours with stirring and cooling to the room temperature so as to obtain a reaction product.

(4) The reaction product was filtrated using a polyvinylidene fluoride (PVDF) membrane with 0.1 μm of pore diameter and was rinsed with methanol and deionized water, followed by removing NMP by drying to obtain Sample 1 (the molar ratio of maleic anhydride to aluminum chloride was 1:1).

Example 2

The chemically-modified graphene of Example 2 (Sample 2) was produced by the same method as that in Example 1 except that the weight of aluminum chloride in step (2) was changed from 1.36 g to 4.08 g (30 mmol) and the molar ratio of maleic anhydride to aluminum chloride was 1:3.

Example 3

The chemically-modified graphene of Example 3 (Sample 3) was produced by the same method as that in Example 1 except that the weight of aluminum chloride in step (2) was changed from 1.36 g to 8.16 g (60 mmol) and the molar ratio of maleic anhydride to aluminum chloride was 1:6.

Example 4

The chemically-modified graphene of Example 4 (Sample 4) was produced by the same method as that in Example 1 except that the maleic anhydride (0.98 g) in step (2) was changed to succinic anhydride (1 g, 10 mmol), and the molar ratio of succinic anhydride to aluminum chloride was 1:1.

Example 5

The chemically-modified graphene of Example 5 (Sample 5) was produced by the same method as that in Example 4 except that the weight of aluminum chloride in step (2) was changed from 1.36 g to 4.08 g, and the molar ratio of succinic anhydride to aluminum chloride was 1:3.

Example 6

The chemically-modified graphene of Example 6 (Sample 6) was produced by the same method as that in Example 4 except that the weight of aluminum chloride in step (2) was changed from 1.36 g to 8.16 g to obtain Sample 6, and the molar ratio of succinic anhydride to aluminum chloride was 1:6.

<Analysis of Crystal Structure>

Figure 2:
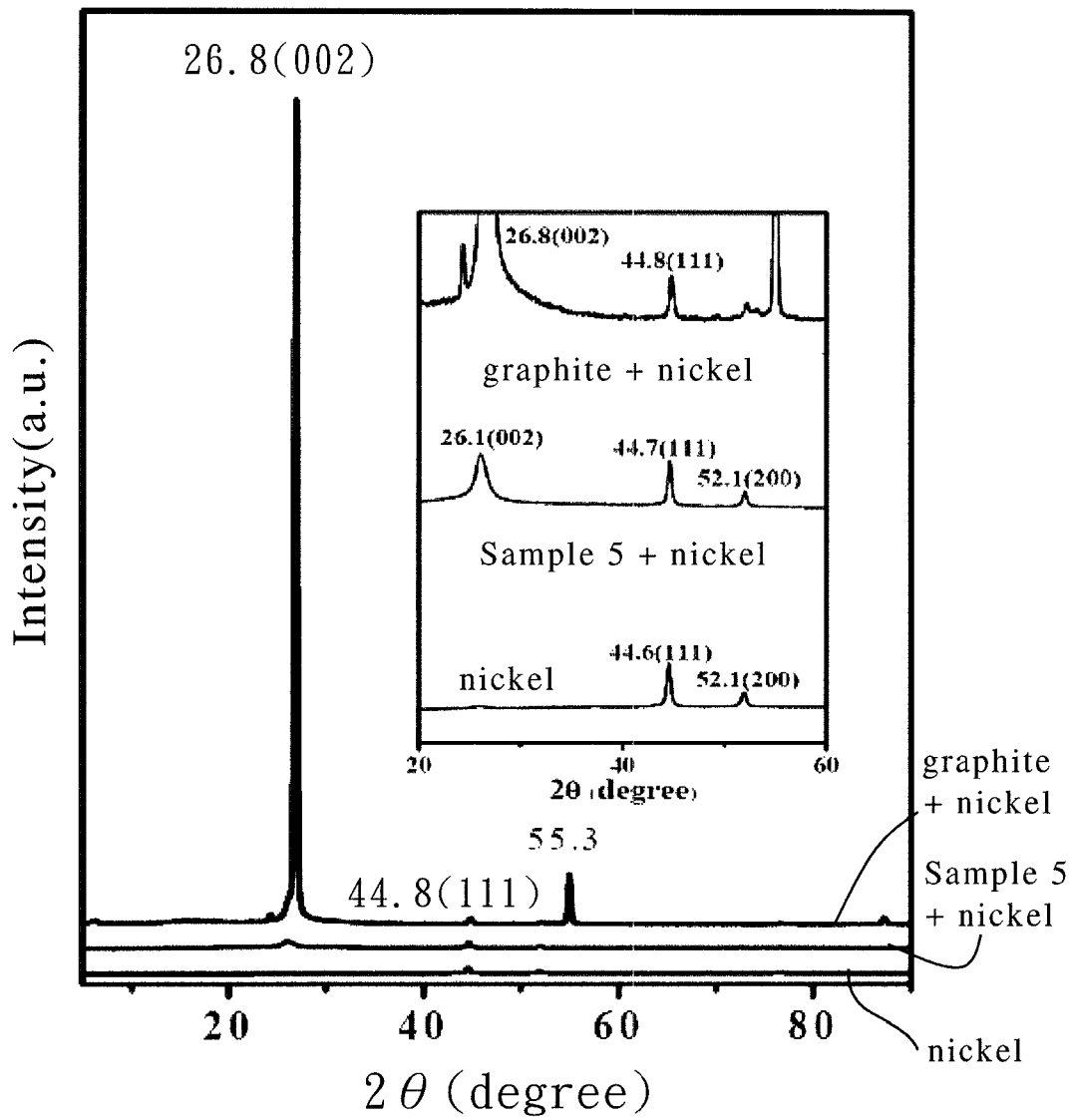
FIG. 2 shows X-ray diffraction (XRD) spectra for the graphite, Sample 5 of Example 5, and nickel, and the inset is an enlarged view at 2θ ranging from 20.0° to 60.0°.

Analyses were conducted on the graphite and Samples 1 to 6 of Examples 1 to 6 using X-ray diffractometer (XRD, Simens, D5005). 15 wt % of nickel was added as a reference basis for comparison of diffraction peak intensity. The analysis results of Samples 1 to 6 are generally the same. For example, the X-ray diffraction spectra for Samples 2 and 5 and the graphite are shown respectively in FIGS. 1 and 2. FIG. 1 shows, from top to bottom, the X-ray diffraction spectra of the graphite (with 15 wt % of nickel), Sample 2 (with 15 wt % of nickel), and nickel, respectively. FIG. 2 shows, from top to bottom, the X-ray diffraction spectra for the graphite (with 15 wt % of nickel), Sample 5 (with 15 wt % of nickel), and nickel, respectively. The insets of FIGS. 1 and 2 are respectively enlarged views of 2θ (diffraction angle) ranging from 20.0° to 60.0° in FIGS. 1 and 2. The graphite shows a significant crystal peak signal at 2θ of 26.8°, which indicates the graphite has a compact multilayer stack structure. However, Samples 2 and 5 have no significant signals at 2θ of 26.8°, which means Samples 2 and 5 are products (graphenes) of the exfoliation of the graphites.

<Analysis of Functional Group Structure>

Analyses were conducted on the graphite and Samples 1 to 6 of Examples 1 to 6, respectively, using Fourier transform infrared spectrometer (FT-IR, Bruker, TENSOR-27).

The analysis results for Samples 1 to 3 are generally the same. The spectrum for each of Samples 1 to 3 shows a broad absorption peak at 3426 $cm^{-1}$, which indicates stretching vibration of O—H, and a strong absorption peak at 1704 $cm^{-1}$, which indicates stretching vibration of C=O of a carboxyl group. However, the graphite shows no absorption peaks at these positions. The results indicate that each of Samples 1 to 3 is grafted with the carboxyl group, i.e., the ring-opened maleic anhydride. In view of the aforementioned analyses, it is verified that Samples 1 to 3 have —CO—CH=CH—COOH groups that are grafted on the graphene layer.

The analysis results for Samples 4 to 6 are generally the same. The spectrum for each of Samples 4 to 6 shows a broad absorption peak at 3247 $cm^{-1}$, which indicates stretching vibration of O—H, an absorption peak at 2945 $cm^{-1}$, which indicates stretching vibration of C—H, and a strong absorption peak at 1702 $cm^{-1}$, which indicates stretching vibration of C=O of a carboxyl group. However, the graphite shows no absorption peaks at these positions. The results indicate that each of Samples 4 to 6 is grafted with the carboxyl group, i.e., the ring-opened succinic anhydride. In view of the abovementioned analyses, it is verified that Samples 4 to 6 have —CO—$CH_2$—$CH_2$—COOH groups that are grafted on the graphene layer.

<Tests for Dispersion>

Each of the graphite and Samples 1 to 6 of Examples 1 to 6 (1 mg) was added in seven solvents, i.e., water, n-hexane, DMF, DMSO, methanol, NMP, and acetone (10 ml), and was subjected to ultrasonic vibration for 1 minute, followed by standing for 1 day. Dispersions of the graphite and Samples 1 to 6 were observed and the test results for Samples 1 to 6 are generally the same. The results for Samples 2 and 5 are used to compare with that of the graphite (see FIG. 3 and Table 1).

TABLE 1

|  | water | n-hexane | DMF | DMSO | methanol | NMP | Acetone |
|---|---|---|---|---|---|---|---|
| graphite | -- | -- | -- | -- | -- | -- | -- |
| Sample 2 | ++ | -- | ++ | + | −+ | ++ | −+ |
| Sample 5 | ++ | -- | ++ | + | −+ | ++ | −+ |

「++」represents completely dispersible;「+」represents mostly dispersible;「−+」represents approximately half dispersible; and「−−」represents not dispersible.

Figure 3:
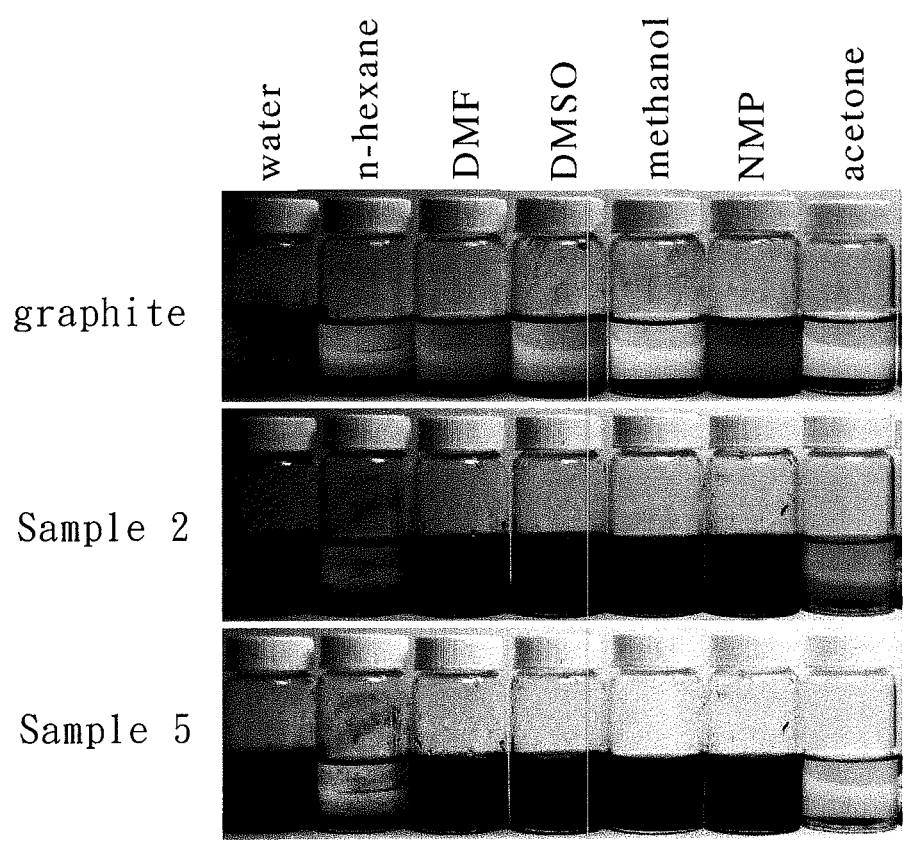
FIG. 3 illustrates dispersion of the graphite, Sample 2 of Example 2, and Sample 5 of Example 5 in seven solvents, i.e., water, n-hexane, N,N-dimethylformamide (DMF), dimethyl sulfoxide (DMSO), methanol, N-methyl-2-pyrrolidone (NMP), and acetone.

It is found from FIG. 3 and Table 1 that the graphite has very poor dispersion in the seven solvents while Samples 2 and 5 have good dispersion ability in water, DMF, DMSO, and NMP. Samples 2 and 5 and the graphite are totally not dispersible in n-hexane.

<Contact Angle Test>

Samples 1 to 6 of Examples 1 to 6 were dropped respectively on cover glasses and dried. Thereafter, water was dropped on each of the dried Samples 1 to 6. Contact angles of the water droplets and the cover glasses were measured and the results are shown in FIG. 4 and Table 2.

TABLE 2

|  | Samples | | | | | |
|---|---|---|---|---|---|---|
| No. | 1 | 2 | 3 | 4 | 5 | 6 |
| Contact angle | 54.06° | 43.76° | 51.12° | 53.41° | 49.93° | 57.96° |

Figure 4:
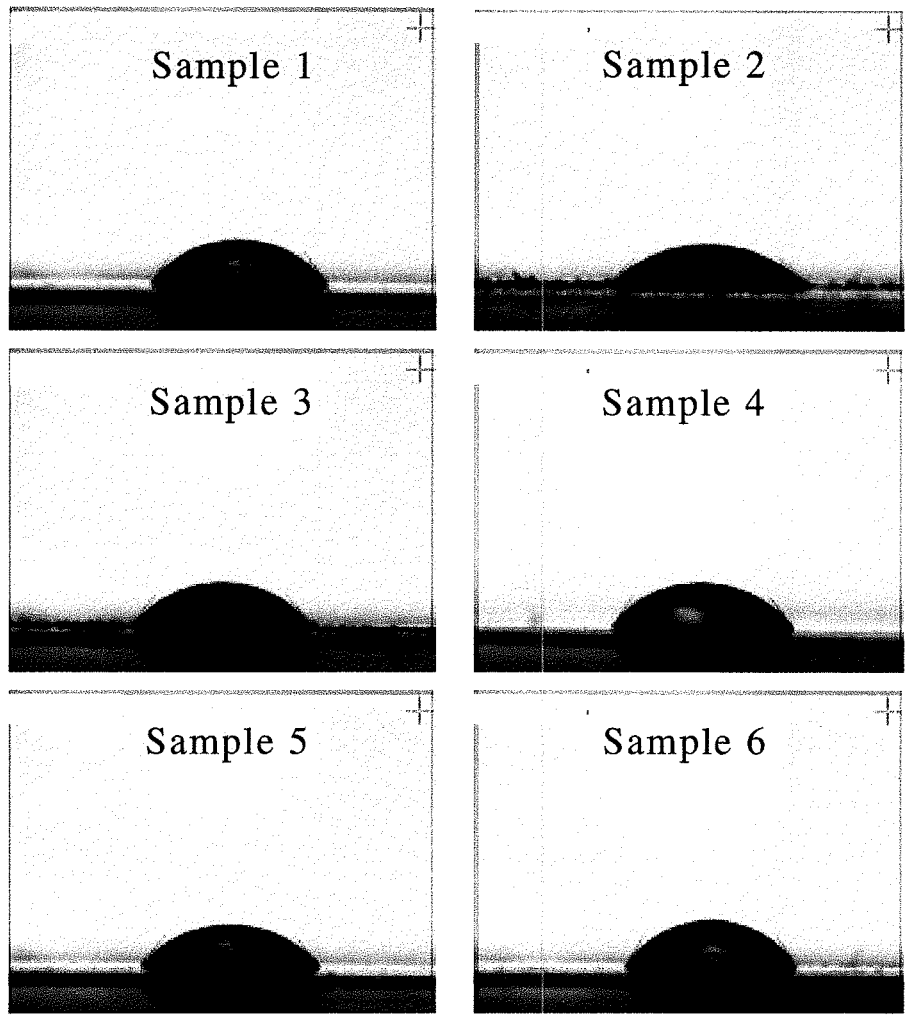
FIG. 4 illustrates the results of test of contact angle for Samples 1 to 6 of Examples 1 to 6.

FIG. 4 and Table 2 show that the contact angles for Samples 1 to 6 range from 43.76° to 57.96°, which represents that Samples 1 to 6 are hydrophilic. The results prove that the graphene has carboxyl group grafted thereon.

<Grafting Ratio Determination>

Structural analyses for Samples 1 to 6 and the graphite were conducted using X-ray photoelectron spectrometer (XPS). The XPS spectra for Samples 1 to 3 are shown in FIGS. 5(b) to 5(d), the XPS spectra of Samples 4 to 6 are shown in FIGS. 6(b) to 6(d), and the XPS spectra for graphite are shown in FIGS. 5(a) and 6(a).

Figure 5:
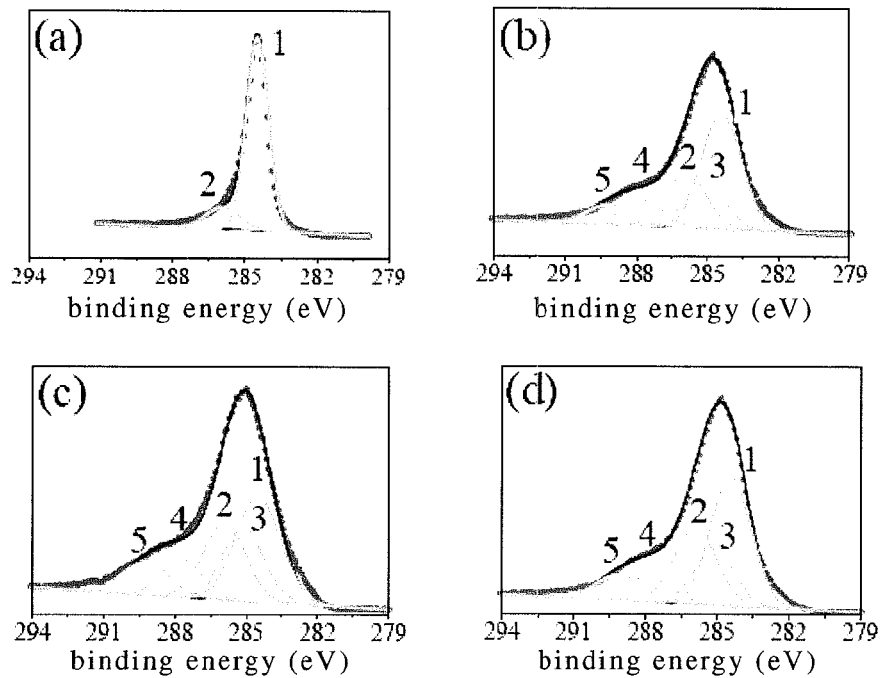
FIGS. 5(*a*) to 5(*d*) are XPS spectra respectively for the graphite and Samples 1 to 3 of Examples 1 to 3.

Comparing FIG. 5(a) with FIGS. 5(b) to 5(d), it is found that, in FIG. 5(a), the graphite shows two carbon characteristic peaks at 284.5 eV (C=C, curve 1 in FIG. 5(a)) and at 285.9 eV (C—O—C, curve 2 in FIG. 5(a)). Further, in FIGS. 5(b) to 5(d), in addition to curves 1 and 2, each of Samples 1 to 3 shows characteristic peaks at 285.1 eV (C=C of the ring-opened maleic anhydride, curve 3 in these figures), 287.7 eV (C=O of the ring-opened maleic anhydride, curve 4), and 289.1 eV (O—C=O of the ring-opened maleic anhydride, curve 5). The results also verify that the graphene has —CO—CH=CH—COOH group grafted thereon. The area ratios of the characteristic peaks 1, 2, 3, 4 and 5 in FIG. 5(b) are 0.44:0.20:0.18:0.09:0.09. From the area ratios of the characteristic peaks 3 to 5, it is known that the grafting ratio of Sample 1 is 9%. Similarly, from the area ratios in FIG. 5(c) and FIG. 5(d), it is known that the grafting ratio of Sample 2 is 10.7%, and the grafting ratio of Sample 3 is 9.3%.

Figure 6:
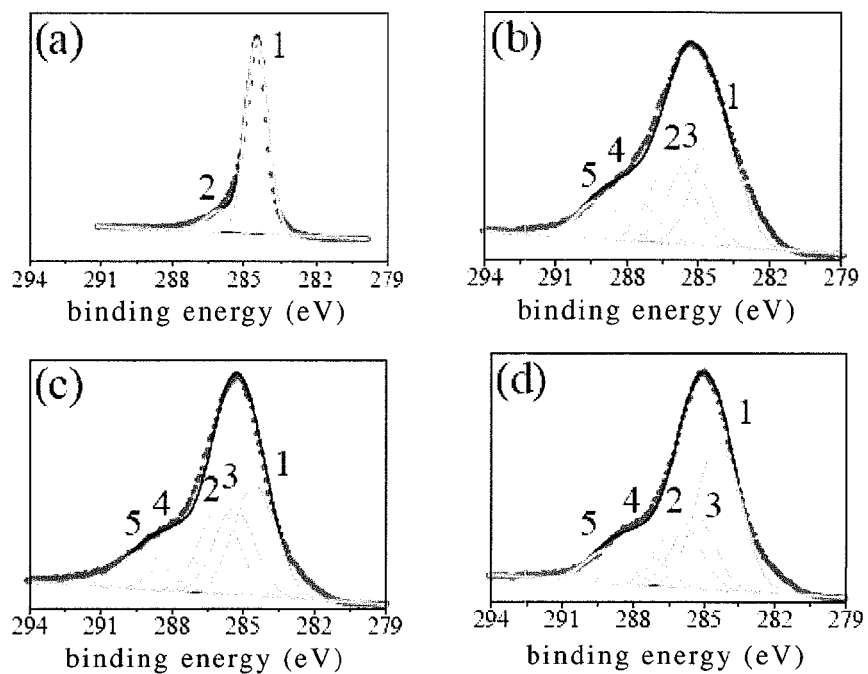
FIGS. 6(*a*) to 6(*d*) are XPS spectra respectively for the graphite and Samples 4 to 6 of Examples 4 to 6.
Figure 7:
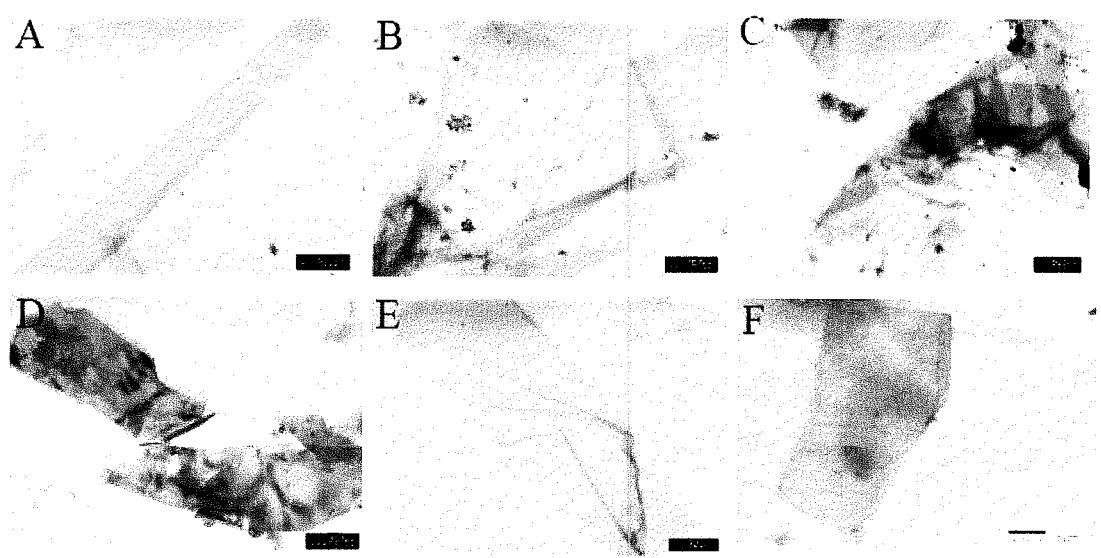
FIG. 7 are TEM photographs illustrating the morphologies of Samples 1 to 6 of Examples 1 to 6, in which A to F are respectively the morphologies of Samples 1 to 6.

Comparing FIG. 6(a) with FIGS. 6(b) to 6(d), it is found that, in FIG. 6(b), in addition to curves 1 and 2, each of Samples 4 to 6 shows characteristic peaks at 285.3 eV (C—C of the ring-opened succinic anhydride, curve 3), 287.4 eV (C=O of the ring-opened succinic anhydride, curve 4), and 289.0 eV (O—C=O of the ring-opened maleic anhydride, curve 5). The results also verify that the graphene has —CO—CH$_2$—CH$_2$—COOH group grafted thereon. The area ratios of the characteristic peaks 1, 2, 3, 4 and 5 in FIG. 6(b) are 0.38:0.22:0.20:0.10:0.10. From the area ratios of the characteristic peaks 3 to 5, it is known that the grafting ratio of Sample 4 is 10%. Similarly, from the area ratios in FIG. 6(c) and FIG. 6(d), it is known that the grafting ratio of Sample 5 is 11.7%, and the grafting ratio of Sample 6 is 10.3%.

<Morphology Observation>

The morphologies of Samples 1 to 6 were observed using transmission electron microscopy (TEM) and the results are shown in FIGS. 7(A) to 7(F), respectively. It is seen from FIGS. 7(A) to 7(F) that the morphology of each of Samples 1 to 6 is a sheet form, rather than a stacked form as the structure of the graphite.

To sum up, the chemically-modified graphene of the present invention can be produced by subjecting directly a cyclic anhydride and graphite to a Friedel-Crafts reaction in the presence of a Lewis acid. The dispersion of the chemically-modified graphene in a polar solvent is significantly better than that of the graphite.

While the present invention has been described in connection with what are considered the most practical and preferred embodiments, it is understood that this invention is not limited to the disclosed embodiments but is intended to cover various arrangements included within the spirit and scope of the broadest interpretation and equivalent arrangements.

What is claimed is:

1. A method for producing a chemically-modified graphene, comprising subjecting a cyclic anhydride and graphite to a Friedel-Crafts reaction in the presence of a Lewis acid,
wherein
   the cyclic anhydride is selected from the group consisting of a maleic anhydride-based compound, a succinic anhydride-based compound, and the combination thereof;
   the Lewis acid is selected from the group consisting of aluminum chloride, aluminum bromide, trifluoroborane, boron trichloride, borontribromide, trimethylboron, iron(III) chloride, magnesium bromide, and combinations thereof; and
   the Friedel-Crafts reaction is conducted in a polar aprotic solvent selected from the group consisting of dimethyl sulfoxide, N-methyl-2-pyrrolidone, N,N-dimethylformamide, N,N-dimethylacetamide, and combinations thereof;
wherein the Friedel-Crafts reaction includes:
   (a) adding the Lewis acid into a cyclic anhydride solution that contains the cyclic anhydride so as to contact the cyclic anhydride with the Lewis acid to form a ring-opened intermediate at a temperature ranging from 70° C. to 120° C.; and
   (b) adding the graphite into the cyclic anhydride solution so as to graft the ring-opened intermediate to the graphite at a temperature ranging from 120° C. to 180° C.

2. The method of claim 1, wherein the cyclic anhydride is selected from the group consisting of maleic anhydride, succinic anhydride, and the combination thereof.

3. The method of claim 1, wherein the molar ratio of the cyclic anhydride to the Lewis acid ranges from 1:0.5 to 1:10.

* * * * *